United States Patent
Akimoto et al.

(10) Patent No.: US 10,632,279 B2
(45) Date of Patent: Apr. 28, 2020

(54) MEDITATION SUPPORT DEVICE AND MEDITATION SUPPORT SYSTEM

(71) Applicant: DENTSU INC., Tokyo (JP)

(72) Inventors: Ken Akimoto, Tokyo (JP); Kana Nakano, Tokyo (JP); Ryoya Sugano, Tokyo (JP); Ryo Makishima, Osaka (JP)

(73) Assignee: DENTSU INC., Tokyo (JP)

( * ) Notice: Subject to any disclaimer, the term of this patent is extended or adjusted under 35 U.S.C. 154(b) by 260 days.

(21) Appl. No.: 15/686,204

(22) Filed: Aug. 25, 2017

(65) Prior Publication Data

US 2018/0056029 A1    Mar. 1, 2018

(30) Foreign Application Priority Data

Aug. 30, 2016    (JP) .................. 2016-168081

(51) Int. Cl.
*A61M 21/02* (2006.01)
*A61M 21/00* (2006.01)
(Continued)

(52) U.S. Cl.
CPC ............. *A61M 21/02* (2013.01); *A61B 5/024* (2013.01); *A61B 5/02438* (2013.01); *A61B 5/165* (2013.01); *A61B 5/486* (2013.01); *A61B 5/7415* (2013.01); *A63B 23/185* (2013.01); *G04F 5/02* (2013.01); *G06F 3/165* (2013.01); *H04R 3/00* (2013.01); *A61B 5/0476* (2013.01); *A61B 2503/12* (2013.01); *A61H 23/02* (2013.01); *A61H 2201/0153* (2013.01); *A61M 2021/0016* (2013.01); *A61M 2021/0022* (2013.01); *A61M 2021/0027* (2013.01); *A61M 2021/0088* (2013.01); *A61M 2205/3553* (2013.01);
(Continued)

(58) Field of Classification Search
CPC ........ A61M 21/00–02; A61M 2230/06; A61M 2230/42; A61B 5/02438; A61B 5/024; A61B 5/486; A61H 2201/0153–1057
See application file for complete search history.

(56) References Cited

U.S. PATENT DOCUMENTS

| 6,036,582 A | 3/2000 | Aizawa et al. |
| 2005/0201424 A1 | 9/2005 | Yoshida et al. |

(Continued)

FOREIGN PATENT DOCUMENTS

| EP | 2311533 A1 | 4/2011 |
| JP | H04-159094 A | 6/1992 |

(Continued)

OTHER PUBLICATIONS

The extended European search report issued in European Patent Application No. 17188083 dated Jan. 18, 2018.
(Continued)

*Primary Examiner* — Thaddeus B Cox
(74) *Attorney, Agent, or Firm* — Pearne & Gordon LLP

(57) ABSTRACT

According to one embodiment of the present disclosure, provided is a meditation support device that is used by being held by hands, the meditation support device including: a sound output module that outputs sound whose volume varies in order to guide timing of respiration; and a vibration generator that generates vibration whose magnitude varies in order to guide timing of respiration.

12 Claims, 11 Drawing Sheets

(51) Int. Cl.
*G04F 5/02* (2006.01)
*A61B 5/024* (2006.01)
*A63B 23/18* (2006.01)
*A61B 5/00* (2006.01)
*A61B 5/16* (2006.01)
*G06F 3/16* (2006.01)
*H04R 3/00* (2006.01)
*A61H 23/02* (2006.01)
*A63B 71/06* (2006.01)
*A61B 5/0476* (2006.01)

(52) U.S. Cl.
CPC ............ *A61M 2205/3561* (2013.01); *A61M 2205/3569* (2013.01); *A61M 2205/3584* (2013.01); *A61M 2205/3592* (2013.01); *A61M 2205/502* (2013.01); *A61M 2205/583* (2013.01); *A61M 2205/586* (2013.01); *A61M 2205/8206* (2013.01); *A61M 2230/06* (2013.01); *A61M 2230/10* (2013.01); *A63B 2071/0655* (2013.01); *A63B 2225/50* (2013.01); *A63B 2230/06* (2013.01)

(56) References Cited

U.S. PATENT DOCUMENTS

| | | | |
|---|---|---|---|
| 2006/0189879 | A1 | 8/2006 | Miyajima et al. |
| 2008/0016621 | A1* | 1/2008 | Chung .................. A47G 9/007 5/636 |
| 2011/0130864 | A1 | 6/2011 | Hirota |
| 2011/0140931 | A1 | 6/2011 | Geurts et al. |
| 2011/0251535 | A1* | 10/2011 | Bender .................. A61M 21/02 601/49 |
| 2015/0011906 | A1* | 1/2015 | Wallach .................. A61K 36/00 600/538 |

FOREIGN PATENT DOCUMENTS

| | | |
|---|---|---|
| JP | H10-340870 A | 12/1998 |
| JP | 2004-276151 A | 10/2004 |
| JP | 2005-152462 A | 6/2005 |
| JP | 2005-260176 A | 9/2005 |
| JP | 2007-181648 A | 7/2007 |
| JP | 2008-536648 A | 9/2008 |
| JP | 2011-530756 A | 12/2011 |
| KR | 2013-0132071 A | 12/2013 |
| WO | 2006-113900 A2 | 10/2006 |
| WO | 2009-145082 A1 | 12/2009 |
| WO | 2011/045709 A1 | 4/2011 |
| WO | 2012/042419 A1 | 4/2012 |
| WO | 2012/117376 A1 | 9/2012 |
| WO | 2015/081355 A1 | 6/2015 |

OTHER PUBLICATIONS

Japanese Office Action issued in Japanese Patent Application No. JP2018-101987 dated Jun. 26, 2018.
Japanese Office Action issued in Japanese Patent Application No. JP2016-168081 dated Jul. 3, 2018.
Japanese Office action issued in Japanese Patent Application No. 2016-072546 dated Jul. 16, 2019.

* cited by examiner

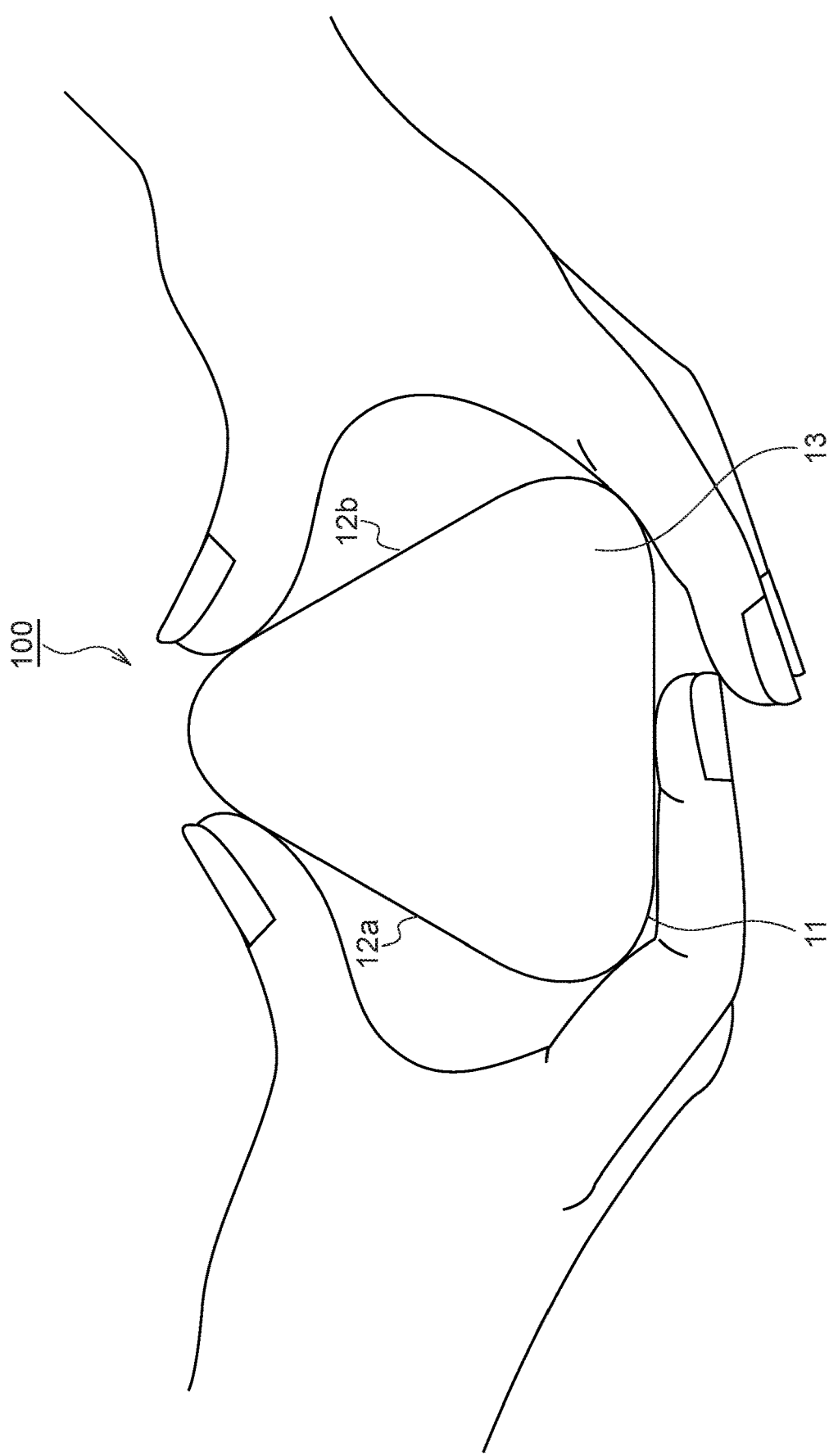

MEDITATION SUPPORT DEVICE AND MEDITATION SUPPORT SYSTEM

CROSS-REFERENCE TO RELATED APPLICATIONS

This application claims the benefit of Japanese Priority Patent Application JP 2016-168081 filed on Aug. 30, 2016, the entire contents of which are incorporated herein by reference.

FIELD

The present disclosure relates to a meditation support device and a meditation support system.

BACKGROUND

In recent years, meditation is gaining attention in the background of obligation of performing stress check in companies, digital fatigue and loss of concentration due to using multiple devices, and the like. It is becoming scientifically obvious that the brain changes when performing meditation and even brief meditation has effects such as stress reduction and concentration power improvement.

However, meditation is not necessarily easy, and there are problems that a correct way to perform meditation is not understood and it is difficult to carry on meditation. The applicant does not know an invention described in a publication that copes with such problems.

The present disclosure is made in view of such problems, and an object of the present disclosure is to provide a meditation support device and a meditation support system that support meditation.

SUMMARY

According to one embodiment of the present disclosure, provided is a meditation support device that is used by being held by hands, the meditation support device including: a sound output module that outputs sound whose volume varies in order to guide timing of respiration; and a vibration generator that generates vibration whose magnitude varies in order to guide timing of respiration.

Preferably, the sound output module and the vibration generator increase the volume of the sound and the magnitude of the vibration, respectively, in a first period among a unit period, and decrease the volume of the sound and the magnitude of the vibration, respectively, in a second period among the unit period.

As an example, the sound output module and the vibration generator may decrease reference levels of the volume of the sound and the magnitude of the vibration, respectively, for each unit period, or increase the reference levels of the volume of the sound and the magnitude of the vibration, respectively, for each unit period.

As another example, the sound output module and the vibration generator may increase the volume of the sound and the magnitude of the vibration, respectively, for each unit period in an earlier first term and thereafter decrease the volume of the sound and the magnitude of the vibration, respectively, for each unit period, or decrease the volume of the sound and the magnitude of the vibration, respectively, for each unit period in an earlier first term and thereafter increase the volume of the sound and the magnitude of the vibration, respectively, for each unit period.

Preferably, the sound output module and the vibration generator vary the volume of the sound and the magnitude of the vibration, respectively according to vital data of a user who holds the meditation support device.

As an example, the sound output module and the vibration generator may increase the volume of the sound and the magnitude of the vibration, respectively, in a first period among a unit period, and decrease the volume of the sound and the magnitude of the vibration, respectively, in a second period among the unit period, and the sound output module and the vibration generator may decrease reference levels of the volume of the sound and the magnitude of the vibration, respectively, with a variation amount according to the vital data for each unit period, or increase the reference levels of the volume of the sound and the magnitude of the vibration, respectively, with a variation amount according to the vital data for each unit period.

As another example, the sound output module and the vibration generator may increase the volume of the sound and the magnitude of the vibration, respectively, in a first period among a unit period, and decrease the volume of the sound and the magnitude of the vibration, respectively, in a second period among the unit period, and the sound output module and the vibration generator may increase reference levels of the volume of the sound and the magnitude of the vibration, respectively, for each unit period in an earlier first time and thereafter decrease the reference levels of the volume of the sound and the magnitude of the vibration, respectively, with a variation amount according to the vital data for each unit period, or decrease reference levels of the volume of the sound and the magnitude of the vibration, respectively, for each unit period in an earlier first time and thereafter increase the reference levels of the volume of the sound and the magnitude of the vibration, respectively, with a variation amount according to the vital data for each unit period.

The meditation support device may further include a controller that determines whether a meditation state is good according to the vital data, wherein the sound output module and the vibration generator may vary the volume of the sound and the magnitude of the vibration according to whether the meditation state is good.

As an example, the sound output module and the vibration generator may increase the volume of the sound and the magnitude of the vibration, respectively, in a first period among a unit period, and decrease the volume of the sound and the magnitude of the vibration, respectively, in a second period among the unit period, and the sound output module and the vibration generator may make, comparing to reference levels of the volume of the sound and the magnitude of the vibration in a present unit period, the reference levels of the volume of the sound and the magnitude of the vibration in a following unit period, smaller, respectively when the meditation state is good, and make, comparing to the reference levels of the volume of the sound and the magnitude of the vibration in a present unit period, the reference levels of the volume of the sound and the magnitude of the vibration in a following unit period, greater, respectively when the meditation state is not good.

The meditation support device may further include a vital sensor that detects the vital data.

Preferably, a housing of the meditation support device includes a bottom face and two slope faces.

Preferably, Japanese cypress is used for at least a part of the meditation support device.

According to another embodiment of the present disclosure, provided is a meditation support system including the meditation support device; and a vital sensor that detects vital data of a user who holds the meditation support device.

BRIEF DESCRIPTION OF DRAWINGS

FIG. 1D is a diagram showing a usage state of the meditation support device according to the first embodiment.

DESCRIPTION

Hereinafter, embodiments will be described in detail with reference to the drawings.

First Embodiment

Figure 1A:
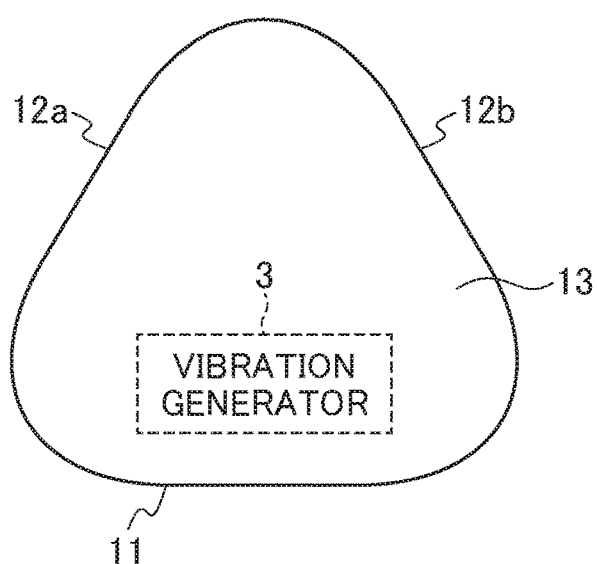
FIG. 1A is a front view of a meditation support device according to a first embodiment.
Figure 1B:
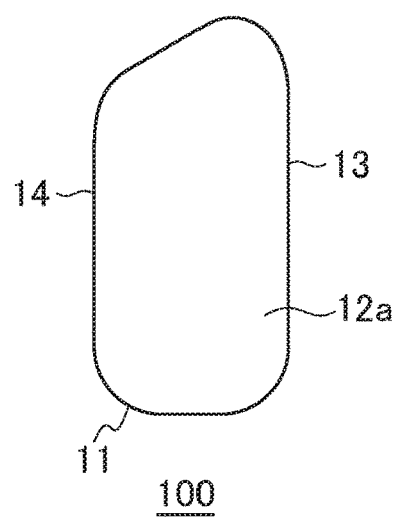
FIG. 1B is a side view of the meditation support device according to the first embodiment.
Figure 1C:
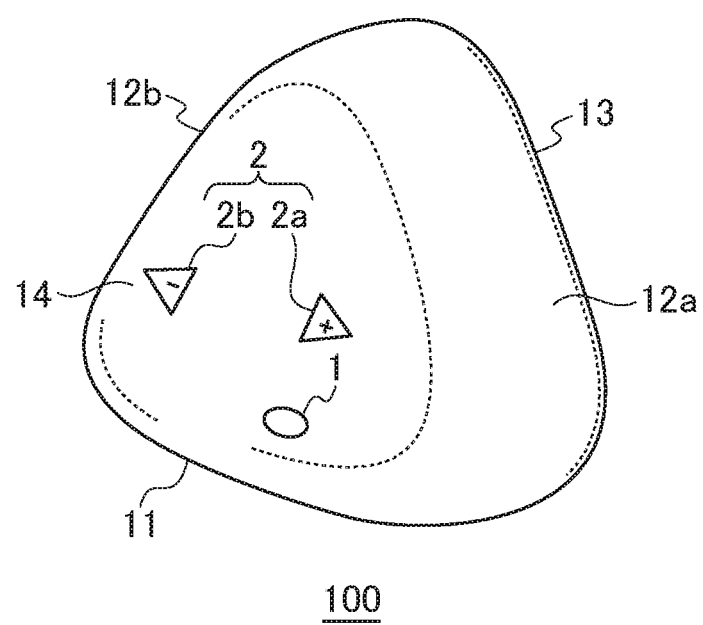
FIG. 1C is a back perspective view of the meditation support device according to the first embodiment.

FIGS. 1A to 1C are a front view, a side view, and a back perspective view, respectively, of a meditation support device 100 according to a first embodiment. FIG. 1D is a diagram showing a usage state of the meditation support device 100.

During normal meditation, four fingers other than the thumb of each hand are overlapped and the thumbs are touched together above the overlapped fingers to form Hokkai-Join (see FIG. 1D). The meditation support device 100 is used by being fitted into a central space of the Hokkai-Join. Specifically, a housing of the meditation support device 100 has a bottom face 11 which comes into contact with the fingers other than the thumbs in the Hokkai-Join and two slope faces 12a and 12b which come into contact with the left and right thumbs, respectively. Owing to such a shape, the fingers fit the meditation support device 100 during meditation.

More specifically, the housing of the meditation support device 100 has the bottom face 11, the two slope faces 12a and 12b extending from both ends of the bottom face 11, a front face 13, and a rear face 14 smaller than the front face 13. The front face 13 and the rear face 14 has a substantially triangular shape having a base and two oblique sides, more accurately, has a so-called Onigiri shape formed by rounding the corners of a triangle. The bottom face 11 is connected to the base of the front face 13 and the base of the rear face 14. Each of the two slope faces 12a and 12b is connected to an oblique side of the front face 13 and an oblique side of the rear face 14, respectively to form side faces. In the present description, a surface that faces a user during meditation is called the rear face 14.

Although a user has nothing during meditation, when the user practices meditation while holding such a meditation support device 100 with his or her hands, the user focuses his or her attention on their lower abdomen, so that the user is urged to have a correct posture in which the user puts strength into his or her lower abdomen (choshin).

It is preferable to use a lumber such as Japanese cypress that exhibits a relaxation effect by specific odor for at least a part (preferably, for the housing) of the meditation support device 100. However, a resin or the like may be used to reduce cost.

The meditation support device 100 includes a sound output module 1 provided, for example, on the rear face 14 and a sound volume adjuster 2 for a user to adjust a sound volume to be outputted (see FIG. 1C).

The sound output module 1 is typically an earphone insertion port, but may be a speaker. The sound output module 1 outputs BGM such as sound of waves, wind blowing through trees, and singing bowl in addition to arbitrary music in order to guide the timing of respiration during meditation (chosoku). The sound output module 1 may output a guidance voice supervised by an expert.

The sound volume adjuster 2 includes a button 2a for increasing the sound volume and a button 2b for decreasing the sound volume.

The meditation support device 100 further includes a vibration generator 3 provided inside the meditation support device 100. The vibration generator 3 guides the timing of respiration (chosoku) and vibrates the meditation support device 100 by, for example, a built-in vibration motor in order to urge a user to concentrate consciousness (choshin). The generated vibration is transmitted to the fingers.

Although the meditation support device 100 may be a smartphone, it is more preferable that the meditation support device 100 is not a smartphone. This is because if the meditation support device 100 is a smartphone, the user may not be able to concentrate on meditation due to reception of email, activation of application, and the like. That is to say, it is desirable that the meditation support device 100 does not have a receiving function, does not generate sound other than the sound outputted by the sound output module 1, and does not generate vibration other than the vibration generated by the vibration generator 3.

Although not shown in the drawings, the meditation support device 100 may be provided with a wired connection interface such as a USB terminal to be able to transmit and receive data to and from external devices, and a battery that drives the meditation support device 100 may be rechargeable.

Figure 2:
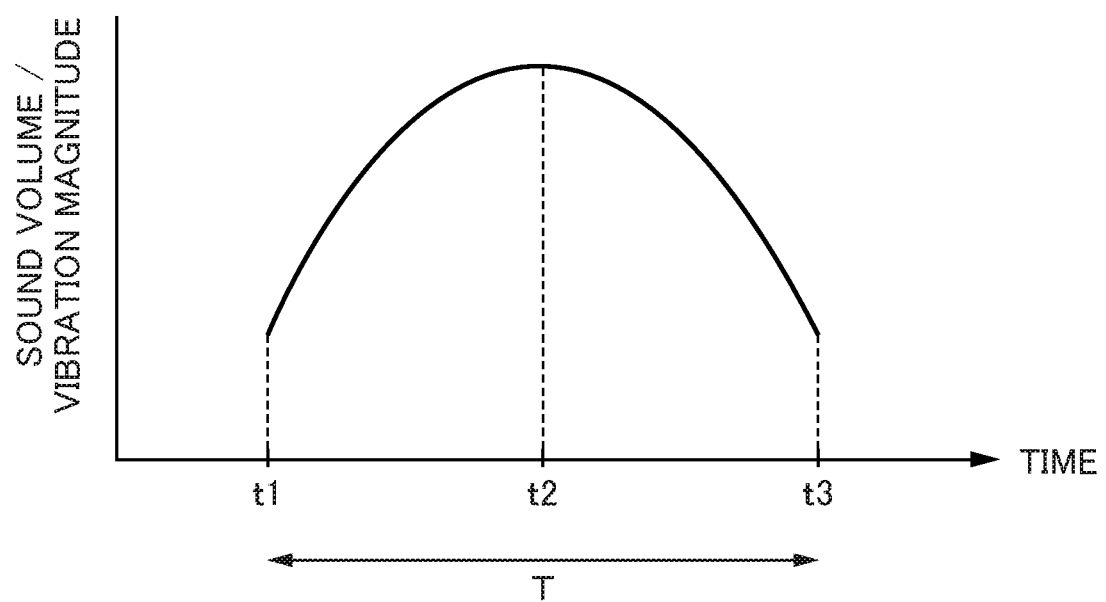
FIG. 2 is a diagram schematically showing a magnitude variation of an outputted sound volume and a generated vibration in a unit period T.

FIG. 2 is a diagram schematically showing a magnitude variation of an outputted sound volume and a generated vibration in a unit period T. The horizontal axis represents time and the vertical axis represents a sound volume (in particular, a sound volume of BGM) and a vibration magnitude. The unit period T includes a period of time in which the sound volume and the vibration gradually increase so as to guide inhaling (hereinafter referred to as an inhaling period) t1 to t2 and a period of time in which the sound volume and the vibration gradually decrease so as to guide exhaling (hereinafter referred to as an exhaling period) t2 to t3. The order of the inhaling period and the exhaling period can be reversed.

In the inhaling period t1 to t2, the sound output module 1 and the vibration generator 3 increase the sound volume and the vibration, respectively. Accordingly, the user may inhale. In the inhaling period t1 to t2, the sound output module 1 may output a guidance voice guiding the user to inhale.

In the exhaling period t2 to t3, the sound output module 1 and the vibration generator 3 decrease the sound volume and the vibration, respectively. Accordingly, the user may exhale. In the inhaling period t2 to t3, the sound output module 1 may output a guidance voice guiding the user to exhale.

In some schools, a period in which the user stops breathing may be provided between the inhaling period t1 to t2 and the exhaling period t2 to t3. In this case, a period in which the sound volume and the vibration are constant may be provided between the inhaling period t1 to t2 and the exhaling period t2 to t3.

As described above, the sound volume outputted by the sound output module 1 and the vibration magnitude generated by the vibration generator 3 vary, so that a breathing rhythm is guided. Specific time periods of the inhaling period t1 to t2 and the exhaling period t2 to t3 may be appropriately set. The time periods may be fixed values or may be adjusted by the user. As an example, the inhaling period t1 to t2 is 5 seconds and the exhaling period t2 to t3 is 10 seconds.

Figure 3A:
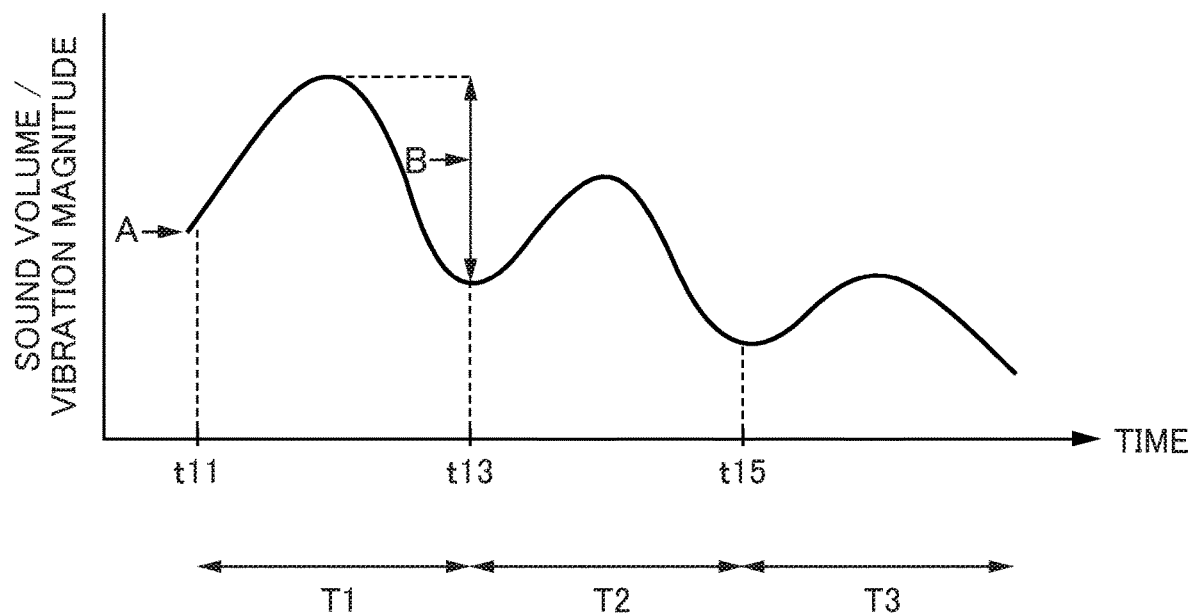
FIG. 3A is a diagram schematically showing a first example of a variation of a sound volume of an outputted sound and a magnitude of a generated vibration for each unit period.

FIG. 3A is a diagram schematically showing a first example of a variation of a sound volume of an outputted sound and a magnitude of a generated vibration for each unit period. In this example, the sound output module 1 and the vibration generator 3 decrease reference levels of the sound volume and the vibration magnitude, respectively, for each of unit periods T1, T2, and T3. The reference levels are, for example, the sound volume and the vibration magnitude at each initial time t11, t13, and t15 of each unit period T1, T2, and T3 (arrow A in FIG. 3A) or an average value of a maximum sound volume (maximum vibration magnitude) and a minimum sound volume (minimum vibration magnitude) in each unit period T1, T2, and T3 (arrow B in FIG. 3A).

In FIG. 3A, the minimum sound volume and the maximum sound volume in a certain unit period are smaller than those in a preceding unit period. The minimum sound volume in each unit period decreases until the minimum sound volume reaches a lower limit value (that may be a fixed value or may be determined according to adjustment by the sound volume adjuster 2). The same goes for the vibration.

Figure 3B:
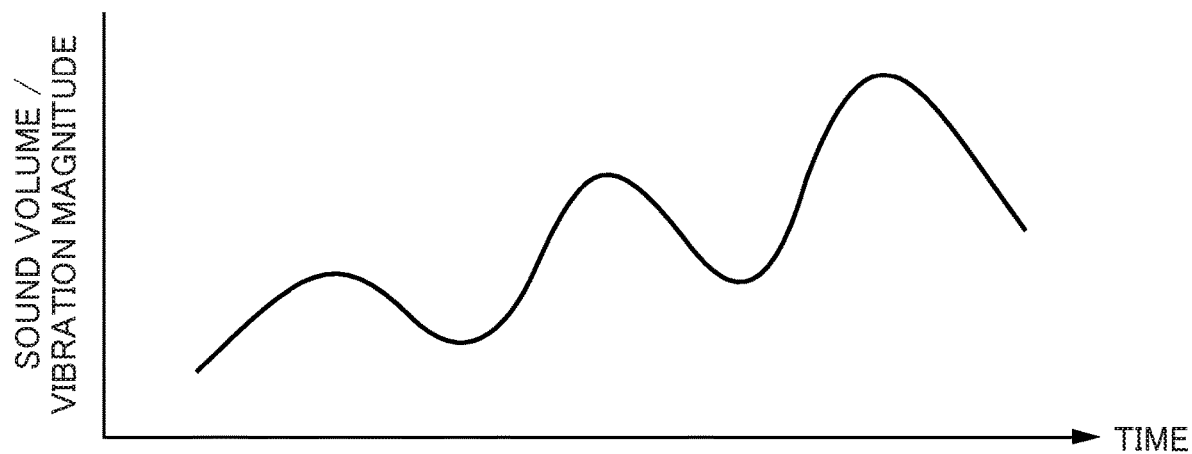
FIG. 3B is a diagram schematically showing a second example of a variation of a sound volume of an outputted sound and a magnitude of a generated vibration for each unit period.

FIG. 3B is a diagram schematically showing a second example of a variation of a sound volume of an outputted sound and a magnitude of a generated vibration for each unit period. In this example, contrary to FIG. 3A, the sound output module 1 and the vibration generator 3 increase the reference levels of the sound volume and the vibration magnitude, respectively, for each unit period.

Figure 3C:
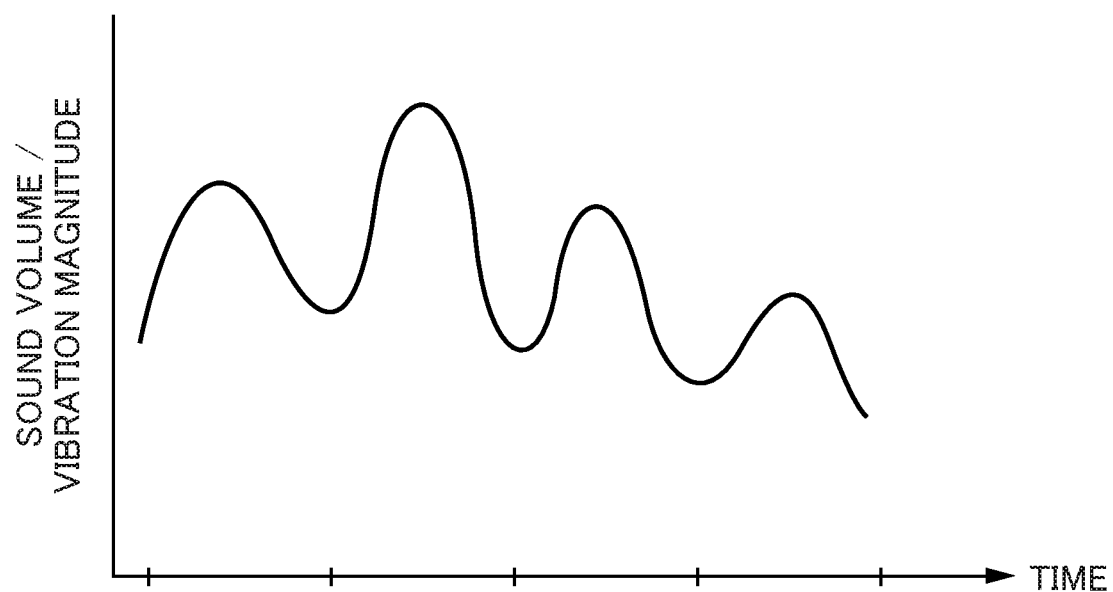
FIG. 3C is a diagram schematically showing a third example of a variation of a sound volume of an outputted sound and a magnitude of a generated vibration for each unit period.

FIG. 3C is a diagram schematically showing a third example of a variation of a sound volume of an outputted sound and a magnitude of a generated vibration for each unit period. In this example, the sound output module 1 and the vibration generator 3 increase the reference levels of the sound volume and the vibration magnitude, respectively, for each unit period in earlier one or plurality of unit periods (for example, about several tens of seconds) and thereafter decrease the reference levels in the same manner as in FIG. 3A.

Figure 3D:
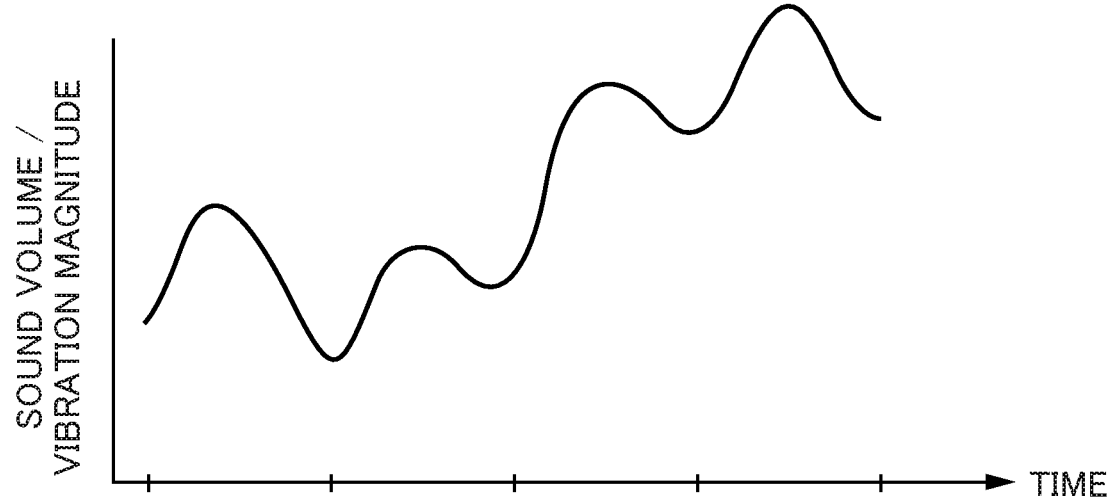
FIG. 3D is a diagram schematically showing a fourth example of a variation of a sound volume of an outputted sound and a magnitude of a generated vibration for each unit period.

FIG. 3D is a diagram schematically showing a fourth example of a variation of a sound volume of an outputted sound and a magnitude of a generated vibration for each unit period. In this example, contrary to FIG. 3C, the sound output module 1 and the vibration generator 3 decrease the reference levels of the sound volume and the vibration magnitude, respectively, for each unit period in earlier one or plurality of unit periods (for example, about several tens of seconds) and thereafter increase the reference levels in the same manner as in FIG. 3B.

The FIGS. 3A to 3D described above are mere examples. To cause a user to be able to habitually practice meditation, the sound output module 1 and the vibration generator 3 may stop output of sound and generation of vibration, respectively, within a relatively short specified period of time (for example, about three minutes), or may continue output of sound and generation of vibration unless the user issues a stop instruction.

As described above, in the first embodiment, choshin is supported when the user holds the meditation support device 100 with his or her hands, chosoku is supported by the sound outputted by the sound output module 1, and chosoku and choshin are supported by the vibration generated by the vibration generator 3. Therefore, it is possible to appropriately support the meditation (in particular, the breathing rhythm).

Second Embodiment

A second embodiment described below relates to a meditation support device including a vital sensor. Hereinafter, differences from the first embodiment will be mainly described.

Figure 4A:
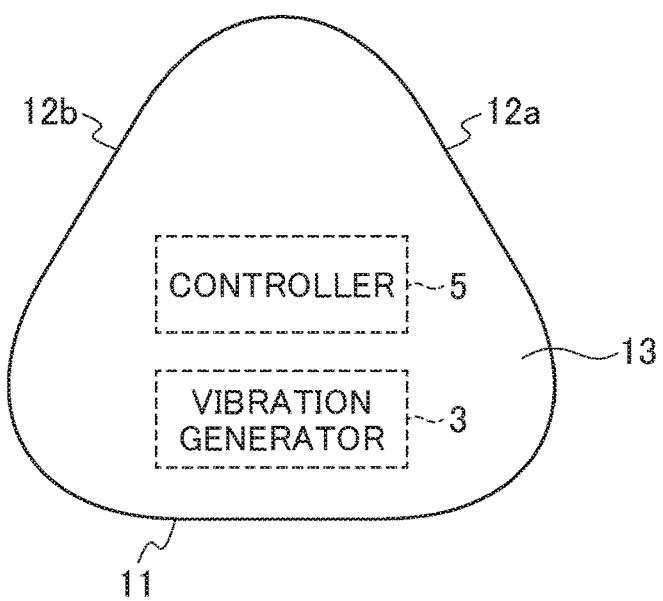
FIG. 4A is a front view of a meditation support device according to a second embodiment.
Figure 4B:
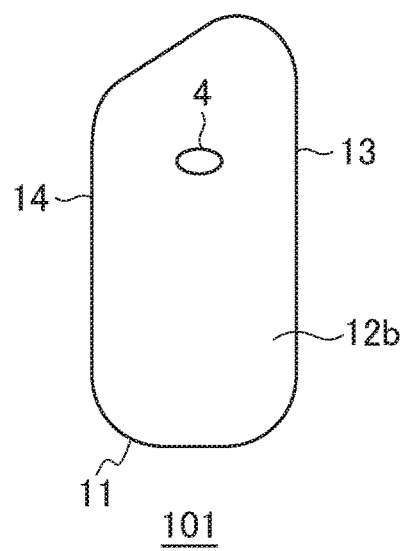
FIG. 4B is a side view of the meditation support device according to the second embodiment.

FIGS. 4A and 4B are a front view and a side view, respectively, of a meditation support device 101 according to the second embodiment. The meditation support device 101 according to the present embodiment further includes a vital sensor 4 (FIG. 4B), which is provided, for example, on a slope face 12b of the meditation support device 101 and detects vital data of a user, and a controller 5 (FIG. 4A) provided inside the meditation support device 101. The better the meditation or the more the stress is reduced, the more a specific change such as a reduction of pulse rate or heartbeat rate appears in the vital data. Therefore, it is possible to grasp a state of meditation from the vital data.

The vital sensor 4 may be a pulse sensor which is provided on the slope face 12b of the meditation support device 101 and detects pulses by being touched by a thumb. Alternatively, the vital sensor 4 may be a heartbeat sensor which is provided on both slope faces 12a and 12b and detects heartbeats by being touched by thumbs of both hands. The vital data to be detected is not particularly limited, and there are various relationships between the vital data and the state of meditation. In the description below, an example will be described in which pulses or heartbeats are detected and the better the state of meditation is, the lower the pulse rate and the heartbeat rate are.

The controller 5 controls the sound output module 1 and the vibration generator 3 according to the vital data detected by the vital sensor 4. Specifically, the sound output module 1 of the present embodiment varies the sound volume according to the vital data and the vibration generator 3 varies the magnitude of vibration according to the vital data.

The controller 5 may cause an LED (not shown in the drawings) provided on the front face of the meditation support device 101 to emit light according to the detected vital data (or a degree of calmness and a degree of stress predicted from the vital data). Further, the controller 5 may transmit the detected vital data and the like through a wired communication (for example, USB) or wireless communication so that the vital data can be managed by and viewed through a smartphone application and a Web site.

Figure 5A:
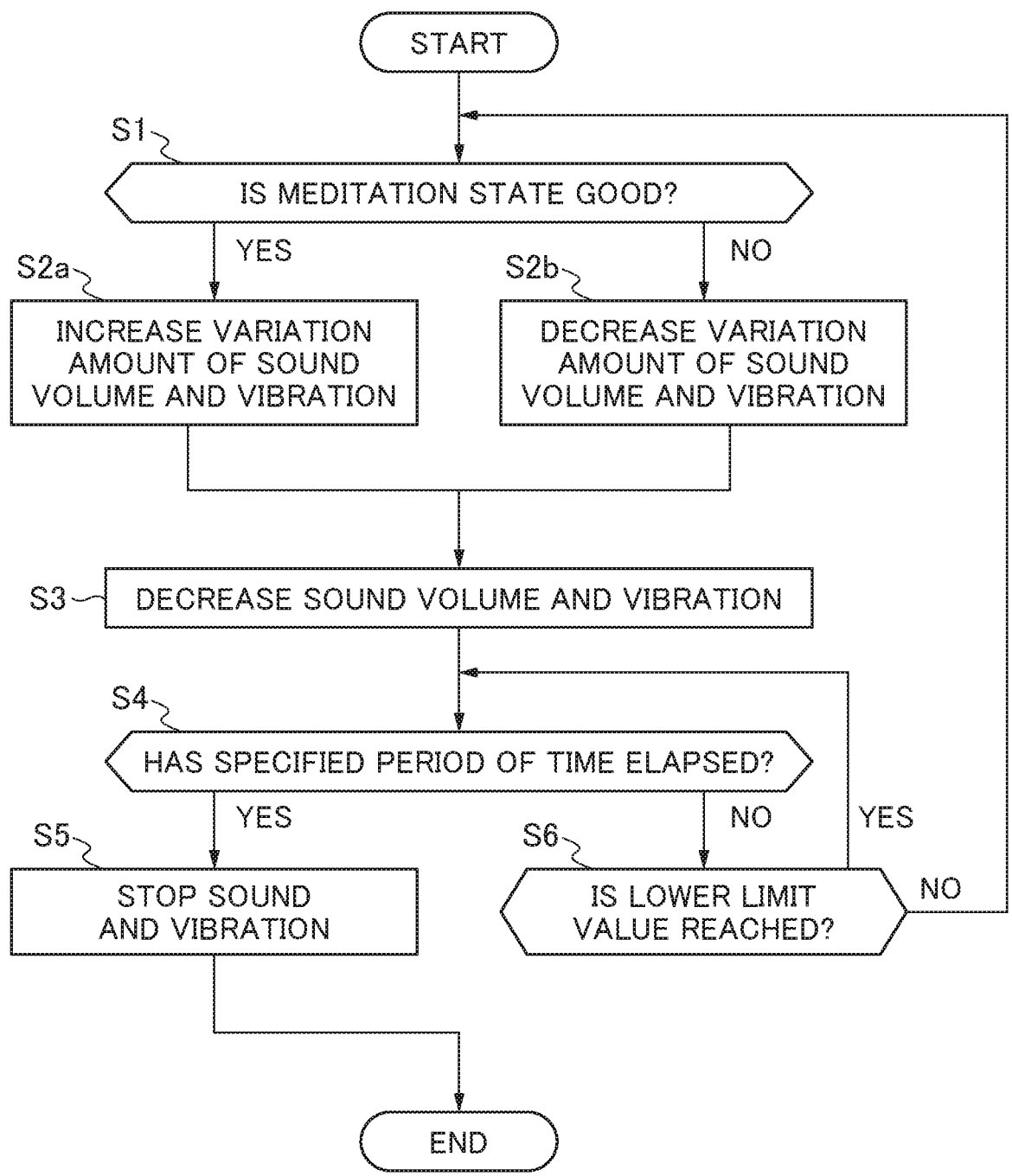
FIG. 5A is a flowchart showing an example of a processing operation of the meditation support device.
Figure 5B:
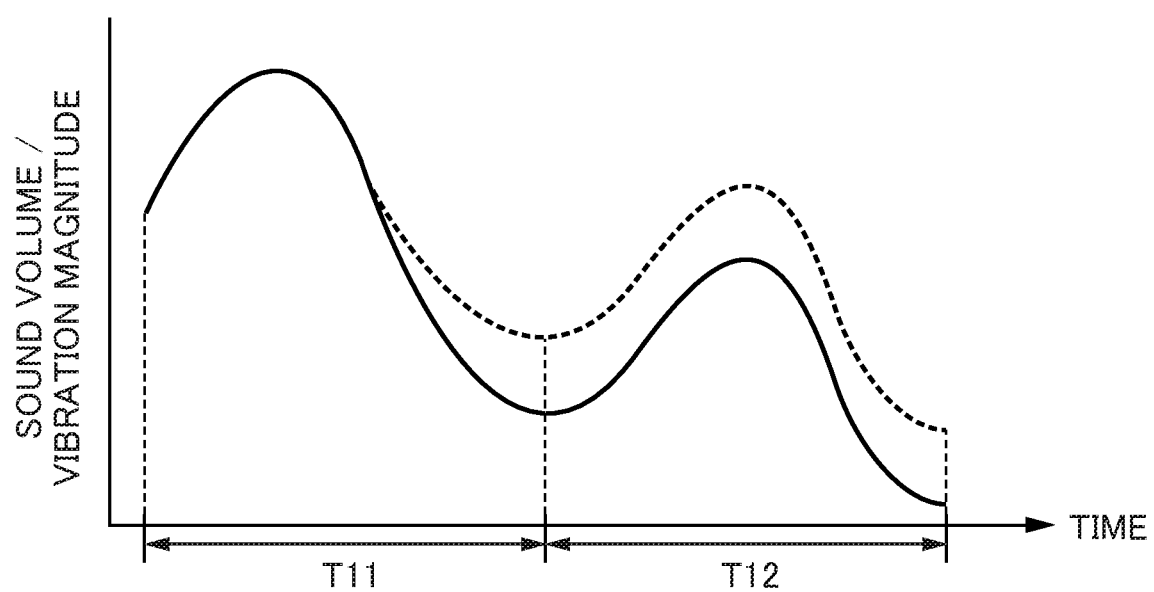
FIG. 5B is a schematic diagram for explaining variations of a sound volume and a vibration magnitude when following the flowchart.

FIG. 5A is a flowchart showing an example of a processing operation of the meditation support device 101. FIG. 5B is a schematic diagram for explaining variations of a sound volume and a vibration magnitude when following the flowchart. This example is an application of FIG. 3A in the first embodiment which decreases reference levels of the sound volume and the vibration magnitude for each unit period.

The controller 5 determines whether the meditation state is good or not based on the vital data (step S1 in FIG. 5A). As an example, the controller 5 can perform the determination by comparing the vital data with a predetermined threshold value. More specifically, the controller 5 may determine that the meditation state is good when the pulse rate or the heartbeat rate is smaller than or equal to a predetermined value and may determine that the meditation state is not good when the pulse rate or the heartbeat rate is greater than the predetermined value. As another example, the controller 5 may compare the vital data detected previously with the vital data detected currently and determine that the meditation state is good when the vital data varies in a preferable manner (for example, when the pulse rate or the heartbeat rate decreases).

When it is determined that the meditation state is good (YES in step S1), the controller 5 sets a variation amount (decrement width) of the sound volume and the vibration magnitude to a relatively large value (step S2a). When it is determined that the meditation state is not good (NO in step S1), the controller 5 sets the variation amount (decrement width) of the sound volume and the vibration magnitude to a relatively small value (step S2b). The sound output module 1 and the vibration generator 3 decrease the reference levels of the sound volume and the vibration magnitude, respectively, in the next unit period according to the set variation amount (step S3).

As a result, when the meditation state is good, the reference level in a unit period T12 decreases relatively larger than the reference level in the previous unit period T11 (solid line in FIG. 5B). On the other hand, when the meditation state is not good, the reference level in the unit period T12 decreases relatively smaller than the reference level in the previous unit period T11 (dashed line in FIG. 5B).

Here, when a specified period of time has elapsed since output of sound and generation of vibration (YES in step S4), the sound output module 1 and the vibration generator 3 stop the output of sound and the generation of vibration, respectively, (step S5) and the processing operation of the meditation support device 101 ends.

When the specified period of time has not elapsed (NO in step S4), if a minimum value of the sound volume and the vibration does not reach a lower limit value (NO in step S6), step S1 and the following steps are performed again. On the other hand, when if the minimum value of the sound volume and the vibration does not reach the lower limit value (YES in step S6), the sound volume and the vibration do not vary any more and a constant sound volume and a constant vibration are generated until the specified period of time elapses (YES in step S4).

In steps S1, S2a, and S2b in FIG. 5A, the controller 5 may set the variation amount not according to a binary value whether the meditation state is good or not, but according to the meditation state, in other words, the controller 5 may set the variation amount into multiple stages according to the vital data. For example, the better the meditation state (the lower the pulse rate or the heartbeat rate), the larger the variation amount that may be set. Further, it is possible to continue the output of sound and the generation of vibration without setting the specified period of time.

While the example shown in FIGS. 5A and 5B is an application of FIG. 3A, FIG. 3B in the first embodiment, in which the reference levels of the sound volume and the vibration are increased for each unit period, may be applied by the same idea.

Further, FIG. 3C in the first embodiment, in which the reference levels of the sound volume and the vibration are firstly increased and thereafter decreased, may be applied. In this case, for example, the reference levels of the sound volume and the vibration may be firstly increased regardless of the vital data and thereafter the reference levels of the sound volume and the vibration may be decreased by applying the processing of FIG. 5A. Further, FIG. 3D in the first embodiment, in which the reference levels of the sound volume and the vibration are firstly decreased and thereafter increased, may be applied by the same idea.

Figure 6A:
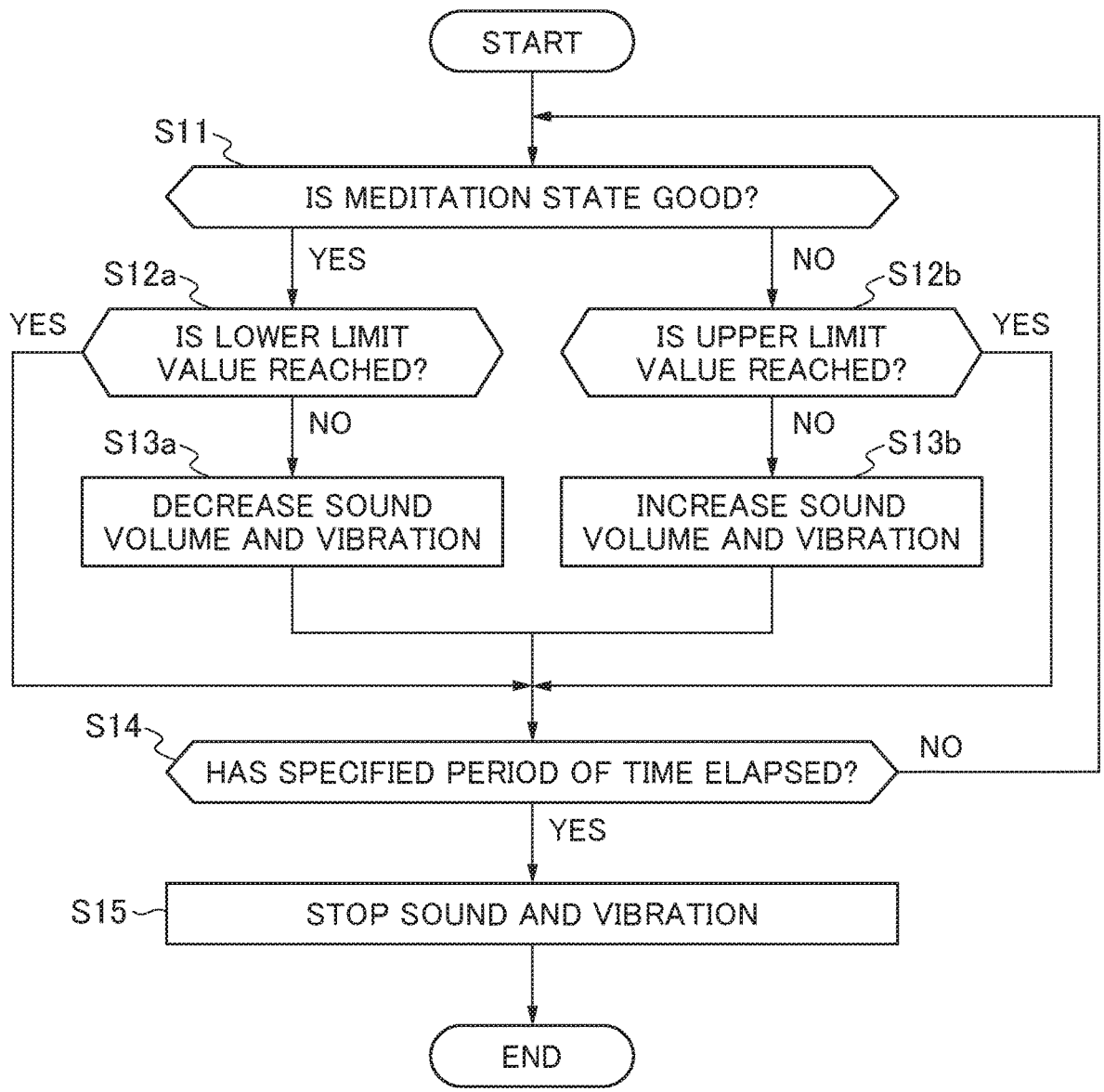
FIG. 6A is a flowchart showing another example of the processing operation of the meditation support device.
Figure 6B:
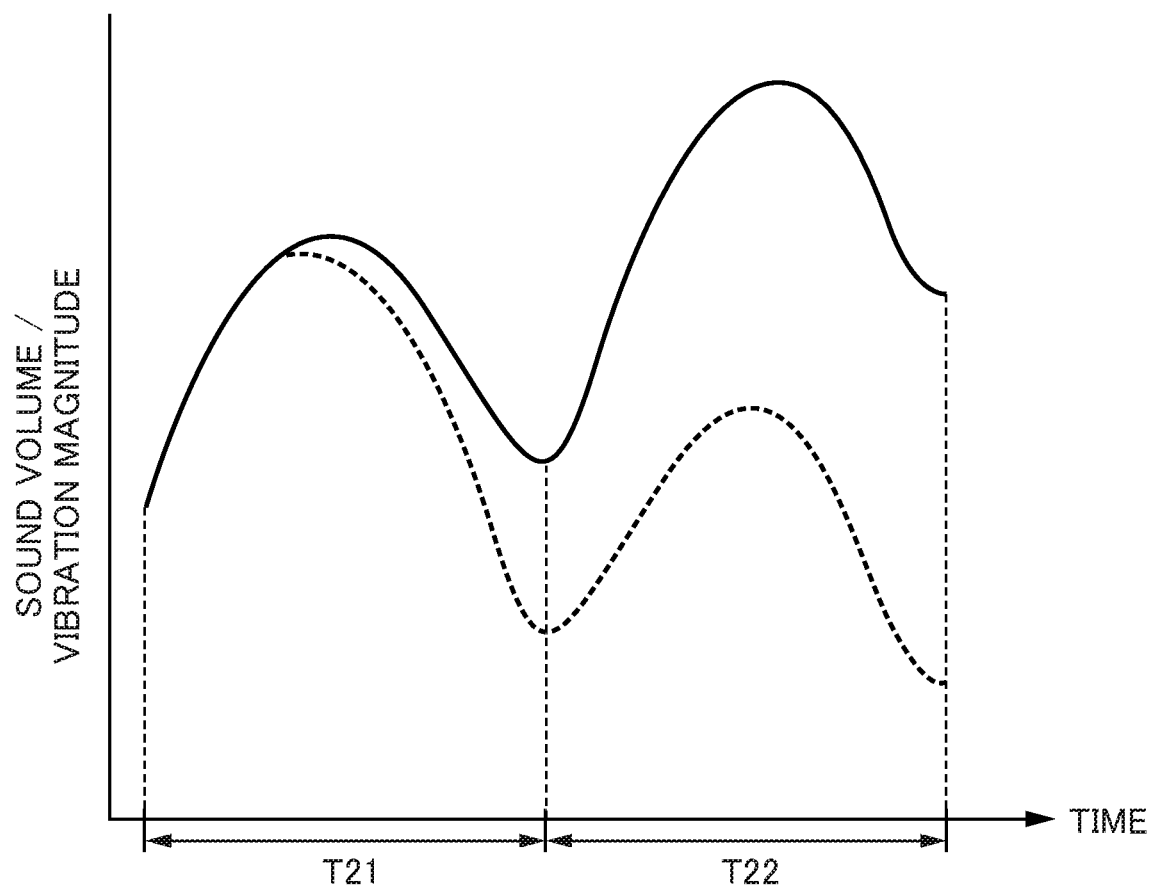
FIG. 6B is a schematic diagram for explaining variations of a sound volume and a vibration magnitude when following the flowchart.

FIG. 6A is a flowchart showing another example of the processing operation of the meditation support device 101. FIG. 6B is a schematic diagram for explaining variations of a sound volume and a vibration magnitude when following the flowchart. This example more strongly interlocks the sound volume and the vibration with the vital data.

The controller 5 determines whether the meditation state is good or not based on the vital data (step S11 in FIG. 6A).

When the meditation state is good (YES in step S11) and the sound volume and the vibration does not reach a lower limit value (NO in step S12a), the controller 5 determines to decrease the reference levels of the sound volume and the vibration. Accordingly, the sound output module 1 and the vibration generator 3 decrease the reference levels of the sound volume and the vibration, respectively, in the next unit period T22 to smaller than those in the current unit period T21 (step S13a, dashed line in FIG. 6B). The better the meditation state (the lower the pulse rate or the heartbeat rate), the larger the decrement width which the controller 5 may set.

On the other hand, when the meditation state is not good (NO in step S11) and the sound volume and the vibration does not reach an upper limit value (NO in step S12b), the controller 5 determines to increase the reference levels of the sound volume and the vibration. Accordingly, the sound output module 1 and the vibration generator 3 increase the reference levels of the sound volume and the vibration, respectively, in the next unit period T22 to greater than those in the current unit period T21 (step S13b, solid line in FIG.

6B). The worse the meditation state (the higher the pulse rate or the heartbeat rate), the larger an increment width which the controller 5 may set.

Here, when a specified period of time has elapsed since output of sound and generation of vibration (YES in step S14), the sound output module 1 and the vibration generator 3 stop the output of sound and the generation of vibration, respectively, (step S15) and the processing operation of the meditation support device 101 ends. When the specified period of time has not elapsed (NO in step S14), step S11 and the following steps are performed again. It is possible to continue the output of sound and the generation of vibration without setting the specified period of time.

As described above, in the second embodiment, the sound volume and the vibration are controlled according to the vital data, so that it is possible to furthermore support the meditation.

In the second embodiment, the vital sensor 4 need not be touched with thumbs, but it may be touched with other regions such as, for example, index fingers that support the meditation support device 101. In this case, the vital sensor 4 may be provided on the bottom face 11.

Further, the vital sensor 4 need not be included in the meditation support device 101, but it may be an external device (for example, a wearable device) and detected vital data may be transmitted to the controller 5 of the meditation support device 101 through wired or wireless communication. In this case, a meditation support system includes the vital sensor 4 and the meditation support device 101. When the vital sensor 4 is an external device, it is possible to detect and use various vital data such as brain waves in addition to pulses and heartbeats.

The above embodiments are described so that a person with an ordinary skill in the technical field to which the invention pertains can implement the invention. Various modified examples of the above embodiments can be naturally made by those skilled in the art, and the technical idea of the invention can be applied to other embodiments. Therefore, the invention is not limited to the described embodiments and should encompass the widest range in accordance with the technical ideas defined by the claims.

100, 101 Meditation support device
1 Sound output module
2 Sound volume adjuster
2a, 2b Button
3 Vibration generator
4 Vital sensor
5 Controller
11 Bottom face
12a, 12b Slope face
13 Front face
14 Rear face

What is claimed is:

1. A meditation support device that is used by being held by hands, the meditation support device comprising:
   a sound output module that outputs sound whose volume varies in order to guide timing of respiration;
   a vibration generator that generates vibration whose magnitude varies in order to guide timing of respiration; and
   a controller that determines whether a meditation state is good according to vital data of a user who holds the meditation support device,
   wherein the sound output module and the vibration generator vary the volume of the sound and the magnitude of the vibration, respectively according to the vital data, and according to whether the meditation state is good,
   wherein the sound output module and the vibration generator increase the volume of the sound and the magnitude of the vibration, respectively, in a first period among a unit period, and decrease the volume of the sound and the magnitude of the vibration, respectively, in a second period among the unit period, and
   the sound output module and the vibration generator:
      make, comparing to reference levels of the volume of the sound and the magnitude of the vibration in a present unit period, the reference levels of the volume of the sound and the magnitude of the vibration in a following unit period, smaller, respectively when the meditation state is good, and
      make, comparing to the reference levels of the volume of the sound and the magnitude of the vibration in a present unit period, the reference levels of the volume of the sound and the magnitude of the vibration in a following unit period, greater, respectively when the meditation state is not good.

2. The meditation support device according to claim 1, wherein the sound output module and the vibration generator:
   increase the volume of the sound and the magnitude of the vibration, respectively, in a first period among a unit period, and
   decrease the volume of the sound and the magnitude of the vibration, respectively, in a second period among the unit period.

3. The meditation support device according to claim 2, wherein the sound output module and the vibration generator:
   decrease reference levels of the volume of the sound and the magnitude of the vibration, respectively, for each unit period, or
   increase the reference levels of the volume of the sound and the magnitude of the vibration, respectively, for each unit period.

4. The meditation support device according to claim 2, wherein the sound output module and the vibration generator:
   increase the volume of the sound and the magnitude of the vibration, respectively, for each unit period in an earlier first term and thereafter decrease the volume of the sound and the magnitude of the vibration, respectively, for each unit period, or
   decrease the volume of the sound and the magnitude of the vibration, respectively, for each unit period in an earlier first term and thereafter increase the volume of the sound and the magnitude of the vibration, respectively, for each unit period.

5. The meditation support device according to claim 1, wherein:
   the sound output module and the vibration generator increase the volume of the sound and the magnitude of the vibration, respectively, in a first period among a unit period, and decrease the volume of the sound and the magnitude of the vibration, respectively, in a second period among the unit period, and
   the sound output module and the vibration generator:
      decrease reference levels of the volume of the sound and the magnitude of the vibration, respectively, with a variation amount according to the vital data for each unit period, or
      increase the reference levels of the volume of the sound and the magnitude of the vibration, respectively, with a variation amount according to the vital data for each unit period.

6. The meditation support device according to claim 1, wherein:
the sound output module and the vibration generator increase the volume of the sound and the magnitude of the vibration, respectively, in a first period among a unit period, and decrease the volume of the sound and the magnitude of the vibration, respectively, in a second period among the unit period, and
the sound output module and the vibration generator:
increase reference levels of the volume of the sound and the magnitude of the vibration, respectively, for each unit period in an earlier first time and thereafter decrease the reference levels of the volume of the sound and the magnitude of the vibration, respectively, with a variation amount according to the vital data for each unit period, or
decrease reference levels of the volume of the sound and the magnitude of the vibration, respectively, for each unit period in an earlier first time and thereafter increase the reference levels of the volume of the sound and the magnitude of the vibration, respectively, with a variation amount according to the vital data for each unit period.

7. The meditation support device according to claim 6, further comprising a vital sensor that detects the vital data.

8. The meditation support device according to claim 6, wherein a housing of the meditation support device comprises a bottom face and two slope faces.

9. The meditation support device according to claim 6, wherein Japanese cypress is used for at least a part of the meditation support device.

10. A meditation support system comprising:
the meditation support device according to claim 6; and
a vital sensor that detects vital data of a user who holds the meditation support device.

11. A meditation support device that is used by being held by hands, the meditation support device comprising:
a sound output module that outputs sound whose volume varies in order to guide timing of respiration; and
a vibration generator that generates vibration whose magnitude varies in order to guide timing of respiration,
wherein a housing of the meditation support device comprises a bottom face and two slope faces, and
wherein an angle between each of the slope faces and the bottom face is 60 degrees.

12. A meditation support device that is used by being held by hands, the meditation support device comprising:
a sound output module that outputs sound whose volume varies in order to guide timing of respiration;
a vibration generator that generates vibration whose magnitude varies in order to guide timing of respiration; and
a controller that controls the volume of the sound output from the sound module and the magnitude of the vibration generated by the vibration generator together,
wherein the controller is configured to:
increase the volume of the sound and the magnitude of the vibration, respectively, in a first period among a unit period, and
decrease the volume of the sound and the magnitude of the vibration, respectively, in a second period among the unit period.

* * * * *